(12) United States Patent
Nagalla et al.

(10) Patent No.: US 12,298,302 B2
(45) Date of Patent: May 13, 2025

(54) SYSTEMS AND METHODS FOR RHEUMATOID ARTHRITIS BIOMARKER DETECTION

(71) Applicant: DIABETOMICS, INC., Hillsboro, OR (US)

(72) Inventors: Srinivasa R. Nagalla, Hillsboro, OR (US); Charles T. Roberts, Portland, OR (US)

(73) Assignee: COVYDX, INC., Hillsboro, OR (US)

( * ) Notice: Subject to any disclaimer, the term of this patent is extended or adjusted under 35 U.S.C. 154(b) by 299 days.

(21) Appl. No.: 17/548,221

(22) Filed: Dec. 10, 2021

(65) Prior Publication Data

US 2022/0187293 A1 Jun. 16, 2022

Related U.S. Application Data

(60) Provisional application No. 63/123,919, filed on Dec. 10, 2020.

(51) Int. Cl.
*G01N 33/564* (2006.01)
*G01N 33/543* (2006.01)

(52) U.S. Cl.
CPC ..... *G01N 33/564* (2013.01); *G01N 33/54388* (2021.08); *G01N 2800/24* (2013.01)

(58) Field of Classification Search
CPC ........... G01N 33/564; G01N 33/54388; G01N 2800/24; G01N 2333/765; G01N 2440/18
See application file for complete search history.

(56) References Cited

U.S. PATENT DOCUMENTS

2010/0055721 A1   3/2010   Lambert et al.

FOREIGN PATENT DOCUMENTS

| WO | 2014164633 A1 | 10/2014 |
| WO | 2015/044453 A1 | 4/2015 |
| WO | 2019/103324 A1 | 3/2019 |

OTHER PUBLICATIONS

Patent Cooperation Treaty: International Search Report and Written Opinion for PCT/SU2021/062928 dated May 16, 2022; 20 pages.
Hefton et al., "Autoantibodies against citrullinated serum albumin in patients with rheumatoid arthritis" Journal of Translational Autoimmunity, Nov. 4, 2019, vol. 2, pp. 1-5.

(Continued)

*Primary Examiner* — Changhwa J Cheu
(74) *Attorney, Agent, or Firm* — Schwabe, Williamson & Wyatt, P.C.

(57) ABSTRACT

Embodiments provide for devices and methods of use for detecting one or more biomarkers of rheumatic disease in a subject. In an example, a method includes detecting citrullinated human serum albumin (HSA) in a biological sample via obtaining the biological sample from a subject, applying the biological sample to a lateral flow device under conditions sufficient for formation of an immunocomplex comprising anti-HSA antibody coupled to citrullinated HSA that is in turn coupled to anti-citrullinated HSA autoantibody, determining a quantity of the immunocomplex, and managing rheumatic disease associated with the subject. In this way, rheumatic disease may be effectively managed based at least in part on amounts of citrullinated HSA detected via rapid point-of-care test methodology.

9 Claims, 6 Drawing Sheets

(56) References Cited

OTHER PUBLICATIONS

Gerlag et al., "Towards prevention of autoantibody-positive rheumatoid arthritis: from lifestyle modification to preventive treatment" Rheumatology (2016) (advanced access publication Sep. 15, 2015), vol. 55, No. 4, pp. 607-614.

Goddard, Gisele Zandman et al.; "A novel bedside test for ACPA: the CCPoint test is moving the laboratory to the rheumatologist's office"; Immunology Research, Humana Press, Inc. US vol. 65, No. 1, Jul. 28, 2016, 6 pages.

SYSTEMS AND METHODS FOR RHEUMATOID ARTHRITIS BIOMARKER DETECTION

CROSS REFERENCE TO RELATED APPLICATION

The present application claims priority to U.S. Provisional Patent Application No. 63/123,919, which was filed Dec. 10, 2020, the disclosure of which is hereby incorporated by reference.

TECHNICAL FIELD

Embodiments herein relate to the field of biomarker detection, and more specifically, to systems and methods of biomarker detection for assessment of rheumatic disease.

BACKGROUND

Rheumatoid arthritis (RA) is an autoimmune disease with unclear etiology, which is characterized by joint inflammation and underlying bone loss. There is currently no cure for RA, but clinical studies indicate that remission of symptoms is more likely when treatment begins early with medications known as disease-modifying antirheumatic drugs (DMARDs), among others. DMARDs may be non-biologic or biologic agents, and biologic DMARDs are usually most effective when paired with a non-biologic DMARD. DMARDs can slow the progression of RA and at least partially save the joints or other tissues from permanent damage. Other relevant treatments include medications (e.g., non-steroidal anti-inflammatory drugs (NSAIDs), steroids, etc.) and physical therapy. If such treatments fail to prevent or slow joint damage, RA surgery may be performed, however surgeries come with risks such as bleeding, infection, and pain, and it is thus desirable to avoid surgery wherever possible.

However, while early treatment is advantageous, early diagnosis of RA is complicated by the fact that known biomarkers may not conclusively identify a patient suffering or prone to developing RA due to a lack of robust biomarker specificity for RA. Accordingly, improved methodology for early assessment of RA is in need. Further, rapid testing for particular biomarkers may enable an ability to closely track progress to particular therapeutic regimens, which in turn may improve aspects of treatment including but not limited to side effect reduction, cost of therapy reduction, and the like.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION OF DISCLOSED EMBODIMENTS

Figure 1:
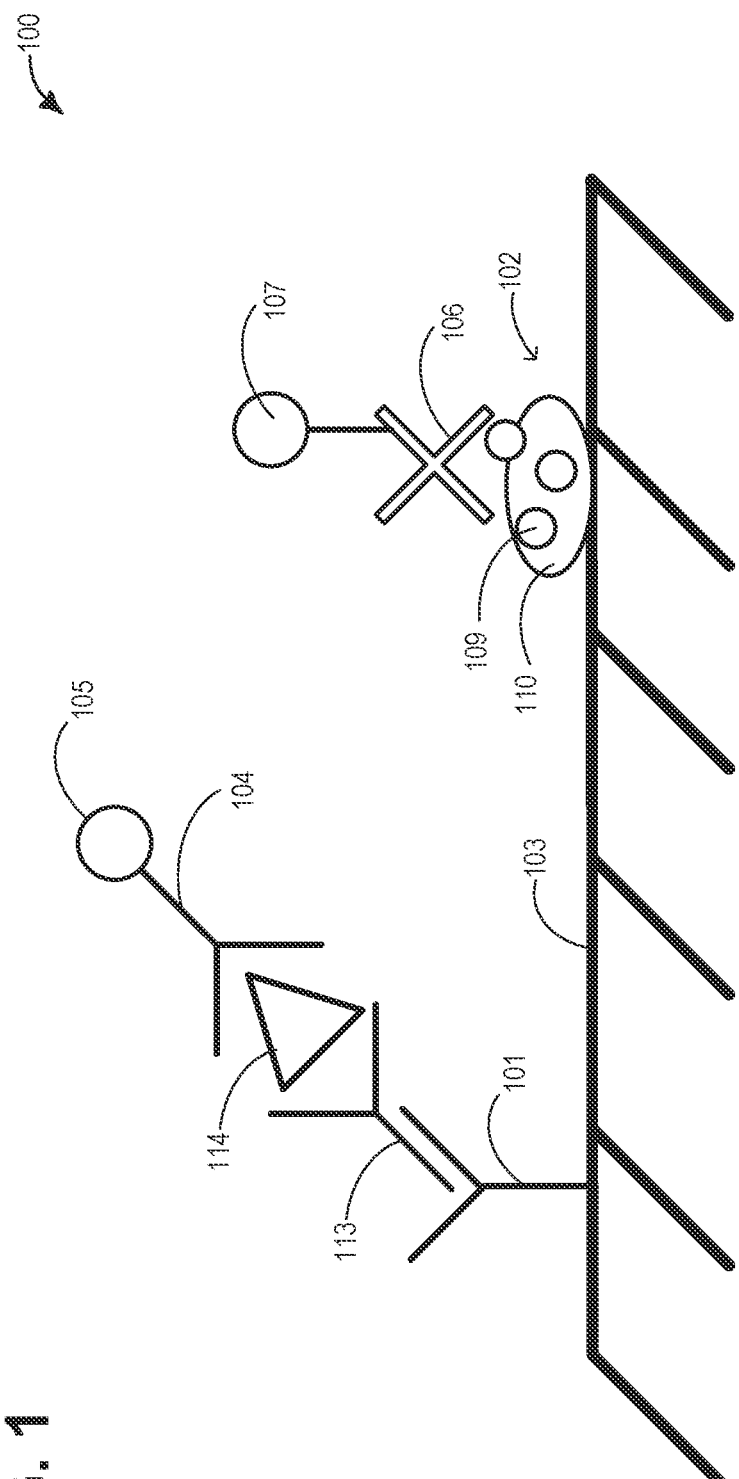
FIG. 1 illustrates a schematic diagram showing an example of a lateral flow assay for detection of anti-citrullinated human serum albumin (HSA) autoantibody-citrullinated HSA complexes in clinical samples.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense.

Production of biomarkers such as rheumatoid factor (RF), anti-citrullinated peptide autoantibodies (ACPAs) and anti-citrullinated human serum albumin (HSA) autoantibodies (ACAs) can occur early in a disease course of RA and in some examples may precede clinical manifestation by a number of years. Exemplary tests for RF measure the amount of RF in blood, and can be measured in at least one of two ways, for example 1) agglutination tests and 2) nephelometry tests. In one example of an agglutination test, a method includes mixing a subject's blood with small rubber beads (e.g., latex) that are covered with human antibodies. The presence of RF causes the beads to clump together (agglutinate), the extent to which can be measured and quantified. In another example of an agglutination test, a method includes mixing a subject's blood with a sheep's red blood cells that have been covered with rabbit antibodies. If RF is present, the red blood cells clump together.

In a nephelometry test, a subject's blood is mixed with antibodies that cause the blood to clump if RF is present. Detection may be via laser-light. Specifically, the test monitors for an amount of light being blocked by the blood sample when laser light is shone onto the sample. Higher levels of RF are associated with greater clumping and a cloudier sample that results in less light passing through a tube that comprises the sample. Other tests for RF have been developed, including enzyme-linked immunosorbent assays (ELISAs) and radioimmune assays (RIAs).

Most currently available ACPA assays comprise kits employing a substrate derived from a synthetic cyclic citrullinated peptide, but differ in incubation time, volume and dilution of serum, type of conjugate and of enzymatic substrate, and range of units reported and thresholds for positive results. Newer assays detect non-cyclic citrullinated peptides. Such assays are, in general, based on detection of autoantibodies by ELISA, microparticle enzyme immunoassay (MEIA), or immunoenzyme fluorimetry.

Although RF is detectable in a majority of RA patients, it is also seen in other connective tissue diseases such as systemic lupus erythematosus (SLE) and Sjögren's syndrome. Similarly, while specificity of ACPA assays for RA compared to healthy individuals is good, there is potential for degraded specificity when other inflammatory disorders are present, including but not limited to psoriatic arthritis, scleroderma, SLE, and seronegative spondyloarthropathies.

There is some evidence that epitopes recognized by RF and ACAP antibodies may be shared in some cases, yet ACPAs appear to exhibit more specificity for RA than RF. ACAs may also be detected in a subset of RA patients. However, because neither RF, ACPA, nor ACA exhibits robust specificity for RA, a multiplex approach employing multiple biomarkers is warranted. Further, with mounting evidence supporting early diagnosis and aggressive treatment to prevent damage and disability, there is a need to easily and reliably test subjects at risk of developing RA, to thereby improve identification and diagnosis of early RA. Accordingly, embodiments herein provide devices and methodology for detecting one or more biomarkers of RA, and managing RA based at least in part on levels of the one or more biomarkers of RA detected in a biological sample using the methods and devices disclosed herein.

I. Overview of Several Embodiments

In one embodiment, a method of detecting anti-citrullinated human serum albumin (HSA) autoantibody in a biological sample comprises obtaining the biological sample from a subject, and applying the biological sample to a lateral flow device under conditions sufficient for formation of an immunocomplex comprising anti-HSA antibody coupled to citrullinated HSA that is in turn coupled to anti-citrullinated HSA autoantibody. The method further includes detecting a quantity of the immunocomplex, and managing rheumatic disease associated with the subject.

In examples, the biological sample is serum or plasma. The anti-HSA may be coupled to a detectable label, for example a colloidal gold particle although other detectable labels are within the scope of this disclosure as discussed infra.

In examples, detecting the quantity of the immunocomplex may be via a reader configured with an image analysis system. Detecting the quantity of the immunocomplex may further comprise quantifying relative amounts of the immunocomplex to a control complex.

In examples, the control complex may comprise streptavidin coupled to a detectable label. The detectable label may be a colloidal gold particle, although other detectable labels are within the scope of this disclosure. In examples, the streptavidin coupled to its detectable label may be captured via the lateral flow device by biotin-coupled to a protein (e.g., bovine serum albumin (BSA)).

In examples, the immunocomplex may be captured via the lateral flow device by an antibody cocktail that includes anti-human IgA, IgG and IgM antibodies.

In examples, managing rheumatic disease in the subject may be a function of the quantity of the immunocomplex detected. For example, managing rheumatic disease in the subject may include selecting one or more therapeutic agents appropriate to manage rheumatic disease based on the quantity of the immunocomplex detected, and the selecting may include determining an effective amount of the one or more therapeutic agents to appropriately manage rheumatic disease. The one or more therapeutic agents may be selected from aspirin, nonsteroidal anti-inflammatory agents, corticosteroids, disease-modifying antirheumatic drugs (DMARDs), penicillamine, Rituximab (monoclonal anti-CD20 antibody), cyclosporine, Infliximab (monoclonal anti tumor necrosis factor antibody), Leflunomide (pyrimidine synthesis inhibitor), Anakinra (recombinant human interleukin-1 receptor antagonist), Etanercept (protein therapy based on a binding fragment of the tumor necrosis factor alpha receptor), and Adalimumab (monoclonal anti tumor necrosis antibody). In some additional or alternative examples, managing rheumatic disease may include recommending to the subject one or more antirheumatic lifestyle modifications. Furthermore, in some additional or alternative examples, managing rheumatic disease may include performing the method of detecting citrullinated human serum albumin again at a later time, and adjusting the managing of rheumatic disease as a function of the quantity of the immunocomplex detected at the later time. Such a cycle can be repeated any number of times to manage rheumatic disease in the subject.

In examples, managing rheumatic disease reduces at least one sign or symptom associated with rheumatic disease. The rheumatic disease may be RA.

Another embodiment includes a method of detecting a first biomarker and at least a second biomarker associated with rheumatic disease in a biological sample of a subject. The method may comprise obtaining the biological sample from the subject, and applying the biological sample to a lateral flow device under conditions sufficient for formation of a first immunocomplex comprising at least the first biomarker and a first labeled biomolecule capable of recognizing the first biomarker, and a second immunocomplex comprising at least the second biomarker and a second labeled biomolecule capable of recognizing the second biomarker. In examples, the first biomarker is citrullinated HSA. In examples, the second biomarker is one of rheumatoid factor (RF) and anti-citrullinated peptide antibody (ACAP). The method may further comprise detecting a quantity of each of the first immunocomplex and the second immunocomplex, and managing rheumatic disease associated with the subject.

In examples, the method may further comprise, via the lateral flow device, detecting a third biomarker that is the other of RF or ACAP by applying the biological sample to the lateral flow device under conditions additionally sufficient for formation of a third immunocomplex comprising at least the third biomarker and a third labeled biomolecule capable of recognizing the third biomarker.

In examples, detecting the quantity of each of the first immunocomplex and the second immunocomplex further comprises additionally detecting a quantity of the third immunocomplex, and managing rheumatic disease associated with the subject.

In examples, managing rheumatic disease in the subject may be a function of a relative quantity of at least two of each of the first immunocomplex, the second immunocomplex and/or the third immunocomplex with respect to one another.

In examples, managing rheumatic disease in the subject may be a function of a relative quantity of each of the first immunocomplex, the second immunocomplex and the third immunocomplex with respect to one another.

In examples, managing rheumatic disease in the subject may further comprise selecting one or more therapeutic agents appropriate to manage rheumatic disease, and the selecting may include determining an effective amount of the one or more therapeutic agents in order to appropriately mange rheumatic disease. The one or more therapeutic agents may be selected from aspirin, nonsteroidal anti-inflammatory agents, corticosteroids, disease-modifying antirheumatic drugs (DMARDs), penicillamine, Rituximab (monoclonal anti-CD20 antibody), cyclosporine, Infliximab (monoclonal anti tumor necrosis factor antibody), Leflunomide (pyrimidine synthesis inhibitor), Anakinra (recombinant human interleukin-1 receptor antagonist), Etanercept (protein therapy based on a binding fragment of the tumor necrosis factor alpha receptor), and Adalimumab (monoclonal anti tumor necrosis antibody).

In examples, managing rheumatic disease may further comprise recommending to the subject one or more antirheumatic lifestyle modifications.

In examples, managing rheumatic disease may further comprise performing the method of detecting the first biomarker and at least the second biomarker again at a later time, and adjusting the managing of rheumatic disease as a function of the quantity of at least two of the first immunocomplex, the second immunocomplex, and/or the third immunocomplex detected at the later time.

In examples, managing rheumatic disease reduces at least one sign or symptom associated with rheumatic disease. The rheumatic disease may be RA, for example.

In yet another embodiment, a lateral flow device capable of reporting a level of citrullinated human serum albumin (HSA) bound to anti-citrullinated HSA autoantibodies in a biological sample obtained from a subject comprises a sample pad for receiving the biological sample, a conjugate pad that includes an anti-HSA antibody coupled to a first detectable label and a first control biomolecule coupled to a second detectable label, and a capture pad that includes a test line and a control line. The test line may include one or more immobilized biomolecules capable of recognizing the anti-citrullinated HSA autoantibodies, and the control line may include a second control biomolecule capable of binding (e.g., recognizing) the first control molecule.

In examples, the first detectable label and the second detectable label may be the same. In other examples, the first detectable label and the second detectable label may be different.

In examples, the first detectable label and the second detectable label may be selected from fluorescent tags/particles, enzymatic linkages, radioactive isotopes, microspheres, and nanoparticles.

In examples, the one or more immobilized biomolecules capable of recognizing anti-citrullinated HSA autoantibodies may comprise an antibody cocktail that includes anti-human IgA, IgM and IgG.

In examples, the first control biomolecule may be streptavidin. The second control biomolecule may be biotin coupled to a protein (e.g., bovine serum albumin (BSA)).

In examples, the lateral flow device detects RA in subjects with a sensitivity of about 39% and a specificity of about 99.8%.

II. Terms

Various operations may be described as multiple discrete operations in turn, in a manner that may be helpful in understanding embodiments; however, the order of description should not be construed to imply that these operations are order-dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Animal: Living multi-cellular vertebrate organisms, a category that includes, for example, mammals and birds. The term mammal includes both human and non-human mammals. Similarly, the term "subject" includes both human and veterinary subjects, for example dogs, cats, mice, etc.

Antibody: A polypeptide ligand comprising at least a light chain or heavy chain immunoglobulin variable region which specifically binds an epitope of a protein discussed herein (which can include another antibody), or a fragment of any of these proteins. The term "specifically binds" refers to, with respect to an antigen such as the proteins/peptides discussed herein, the preferential association of an antibody or other ligand, in whole or part, with the protein. A specific binding agent binds substantially only to a defined target, such as protein of interest. Thus, as a non-limiting example, a citrullinated peptide or protein-specific binding agent is an agent that binds substantially to a citrullinated protein or peptide. If an agent, such as an antibody, specifically binds a particular citrullinated peptide or protein, it does not specifically bind other peptides or proteins that are non-citrullinated. A minor degree of non-specific interaction may occur between a molecule, such as a specific binding agent, and a non-target polypeptide. Specific binding can be distinguished as mediated through specific recognition of the antigen.

A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, Antibodies, A Laboratory Manual, Cold Spring Harbor Publications, New York (1988), for a description of immunoassay formats and conditions that can be used to determine specific immunoreactivity.

Antibodies can include a heavy chain and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes recombinant forms such as chimeric antibodies (for example, humanized murine antibodies), heteroconjugate antibodies (such as, bispecific antibodies), etc. See also, Pierce Catalog and Handbook, 1994-1995 (Pierce Chemical Co., Rockford, Ill.); Kuby, Immunology, 3rd Ed., W.H. Freeman & Co., New York, 1997.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making a hybrid antibody-forming cells from a fusion of myeloma cells with immune spleen cells. These fused cells and their progeny are termed "hybridomas." Monoclonal antibodies include humanized monoclonal antibodies.

Anti-citrullinated human serum albumin autoantibodies (ACAs): Refers to autoantibodies that recognize citrullinated human serum albumin (HSA). ACAs comprise a subset of anti-citrullinated protein antibodies (ACPAs).

Anti-citrullinated peptide autoantibody (ACPAs): Autoantibodies with different isotypes usage (e.g., IgG, IgA, IgM) that recognize the nonessential amino acid citrulline in peptides and/or proteins. Citrulline is formed as a result of post-translational modification of arginine, catalyzed by intracellular enzymes known as peptidylarginine deiminases (PADs). The generation of ACPAs appears to be a specific phenomenon for RA and can start years before the onset of disease. Discussed herein, ACPAs include but are not limited to anti-cyclic citrullinated peptide antibodies (anti-CCP).

Autoantibody: Antibodies that react with self-antigens. These antigens may be found in a wide variety of cell types in some examples, be highly specific for particular cell types in other examples, or may comprise circulating antigens throughout a body of an animal. Autoantibodies are formed in an animal's own body, and are capable in examples of directly destroying cells that have the self-antigen on them or can render them more susceptible to white blood cells that in turn can destroy them. Some autoimmune diseases can be caused by autoantibodies.

Autoimmune disease: A disease in which an animal's body attacks parts of its body, including but not limited to joints and skin, as foreign. Examples of autoimmune disease include but are not limited to Rheumatoid arthritis (RA), Psoriasis/psoriatic arthritis, Multiple sclerosis, Type 1 diabetes, Systemic lupus erythematosus (SLE), Inflammatory bowel disease (IBD), Autoimmune vasculitis, Celiac disease, Hashimoto's thyroiditis, Graves disease, Sjögren's syndrome, Pernicious anemia, Myasthenia gravis, Vasculitis, Ankylosing spondylitis, among others.

Antirheumatic agent: Refers to agents used in the therapy of inflammatory arthritis, for example Rheumatoid arthritis. An anti-rheumatic agent can also be used in the therapy of psoriatic arthritis, ankylosing spondylitis, idiopathic juvenile arthritis, among others. Examples of antirheumatic agents include but are not limited to aspirin, nonsteroidal anti-inflammatory agents, corticosteroids, DMARDs, penicillamine, Rituximab (monoclonal anti-CD20 antibody), cyclosporine, Infliximab (monoclonal anti tumor necrosis factor antibody), Leflunomide (pyrimidine synthesis inhibitor), Anakinra (recombinant human interleukin-1 receptor antagonist), Etanercept (protein therapy based on a binding fragment of the tumor necrosis factor alpha receptor), Adalimumab (monoclonal anti tumor necrosis antibody), and the like.

Antirheumatic lifestyle modifications: Changes to lifestyle, habits and practices intended to alleviate the symptoms of rheumatoid arthritis. Examples include changes to physical activity (e.g., increase in exercise), changes that lead to a reduction in body mass index (BMI), reduction or cessation of smoking, increase in vitamin and/or mineral intake (e.g., increased vitamin D intake), reduction in stress levels, increased quality of sleep, and the like.

Binding: A specific interaction between two or more molecules, such as the binding of an antibody and an antigen (for example an antibody to an antigen). In one embodiment, specific binding is identified by a dissociation constant (Kd). In another embodiment, binding affinity is measured by a dissociation rate. In yet another embodiment, a binding affinity is measured by a competition assay.

Contacting: "Contacting" as referred to herein includes in solution and solid phase, for example contacting a blood or serum protein with a test agent. In another example, contacting includes contacting a sample with an antibody, for example contacting a sample that contains a protein of interest. In another example, contacting includes contacting a sample to a sample well/pad of a lateral flow test strip.

Citrullinated: Peptides or proteins which have one or more amino acids that have been deimidated, for example peptides or proteins in which one or more arginine residues have been deimidated to citrulline.

Effective amount: An amount of therapeutic agent that is sufficient to generate a desired response, such as reducing or inhibiting one or more signs or symptoms associated with a condition or disease. When administered to a subject, a dosage will generally be used that will achieve target tissue/cell concentrations. In some examples, an "effective amount" is one that treats one or more symptoms and/or underlying causes of any of a disorder or disease. In a representative example, an "effective amount" is a therapeutically effective amount in which the agent alone or with one or more additional therapeutic agent(s) induces the desired response such as reduction in one or more symptoms associated with RA.

In particular examples, it is an amount of an agent capable of binding CD20 antigen on B cells, to elicit one or more effector functions following the binding, leading to a desired response. In some examples, an effective amount is an amount of a pharmaceutical preparation that alone, or together with a pharmaceutically acceptable carrier or one or more additional therapeutic agents (e.g., methotrexate), induces the desired response.

In one example, a desired response is to increase the subject's survival time and/or improve the subject's quality of life, for example by reducing a number and/or amount of signs/symptoms associated with RA. In another example, a desired response is to increase the subject's survival time and/or improve the subject's quality of life by slowing or eliminating progression of disease, such as slowing or eliminating the progression of RA.

The symptoms and/or underlying cause of a disease, syndrome, etc., do not need to be completely inhibited for the pharmaceutical preparation to be effective. For example, a pharmaceutical preparation may decrease the progression of the disease, syndrome, etc., by a desired amount, for example by at least 10%, at least 20%, at least 50%, at least 60%, at least 70%, at least 80%, at least 90%, at least 95%, at least 98%, or even at least 100%, as compared to the progression typical in the absence of the pharmaceutical preparation.

In another or additional example, it is an amount sufficient to partially or completely alleviate symptoms of the disease (e.g., RA) within the subject. Treatment can involve only slowing the progression of the disease temporarily, but can also include halting or reversing the progression of the disease permanently.

Effective amounts of the agents described herein can be determined in many different ways, such as, for example, assaying for a reduction in of one or more signs or symptoms associated with RA in the subject or measuring the expression level of one or more biological molecules (e.g., RF, ACAP, ACA) known to be associated with RA. Effective amounts also can be determined through various in vitro, in vivo or in situ assays, including the assays described herein.

The disclosed therapeutic agents can be administered in a single dose, or in several doses, for example hourly, daily, weekly, monthly, yearly, during a course of treatment. The effective amount can be dependent on the subject being treated, the severity and type of the condition being treated, and the manner of administration. In some examples, one or more of dosage, frequency of administration, type of agent, etc., can be adjusted depending on changes in signs or symptoms, changes in biomarker levels, etc., associated with RA.

Immunoassay: A biochemical test that measures the presence or concentration of a substance in a sample, such as a biological sample, using the reaction of an antibody to its cognate antigen, for example the specific binding of an antibody to a protein. The presence of antigen and in some examples the amount of antigen present, can be measured.

Inflammation: Refers to a condition that occurs in animals when tissues are injured in some way, causing the damaged cells to release particular chemicals including but not limited to histamine, bradykinin, prostaglandins, and the like. Tissue injury may be caused by bacteria, trauma, toxins, heat, diet, repetitive use, stationary lifestyle, and the like Inflammation may be acute or chronic. Acute inflammation can last anywhere from 1-2 days to 2-6 weeks. Chronic inflammation can continue for months or even years and can have links to various diseases including but not limited to rheumatoid arthritis. Herein, inflammation is used interchangeably with inflammatory response.

Lateral flow assay (LFA): A platform for the detection and quantification of analytes in complex mixtures, including but not limited to urine, saliva, sweat, serum, plasma, whole blood, and the like. Lateral flow assays can be categorized into different types, such as lateral flow immunoassays (LFIAs) in which antibodies are exclusively used as recognition elements, and nucleic acid LFAs, used for the detection of amplicons, which can be formed during a polymerase chain reaction (PCR). The principle of LFAs relies on a liquid sample or its extract containing an analyte of interest moving without the assistance of external forces through a number of zones of a lateral flow test strip, on which molecules that can interact with the analyte are attached. Such interaction molecules can be labeled with a detectable label to facilitate detection of the interaction.

Label: A detectable compound or composition that is conjugated directly or indirectly to another molecule, such as an antibody or other protein/peptide, to facilitate detection of that molecule or a molecule (or complex) to which the labeled molecule is bound. Specific, non-limiting examples of labels include fluorescent tags/particles, enzymatic linkages, radioactive isotopes (for example 14C, 32P, 125I, 3H isotopes and the like), microspheres, nanoparticles, and the like.

In examples, nanoparticles may comprise one or more of metal nanoparticles, magnetic nanoparticles, silica nanoparticles, and latex nanoparticles.

In examples, the fluorescent particles can include one or more of Alexa fluoro 350, 405, 430, 488, 500, 514, 633, 647, 660, 680, 700, cy3, cy5, cy7, ruby (tris (2,2-bipyridyl) ruthenium), FITC (fluoresein isothiocyanate), rhodamine 6G, rhodamine B, TAMRA (6-carboxy-tetramethyl-rhodamine), Texas Red, DAPI (4,6-diamidino -2-phenylindole, and coumarin, or may be time-resolved fluorescence (TRF).

Optional: "Optional" or "optionally" means that the subsequently described event or circumstance can but need not occur, and that the description includes instances where said event or circumstance occurs and instances where it does not.

Patient: As used herein, the term "patient" includes human and non-human animals. The preferred patient for treatment is a human. "Patient" and "subject" are used interchangeably herein.

Pharmaceutical agent: A chemical compound or composition capable of inducing a desired therapeutic (including in some examples a prophylactic effect) when properly administered to a subject. The pharmaceutically acceptable salts of the compounds of this invention include, but are not limited to, those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. This term refers to pharmaceutical agents, pharmaceutical compositions, and drugs acceptable for both human and veterinary uses.

Proteome: A significant portion of proteins in a biological sample at a given time. A "proteomic profile" is a representation of the expression pattern of a plurality of proteins in a biological sample, such as plasma or serum, at a given time.

Rheumatoid arthritis (RA): A disease that causes joint inflammation, pain and underlying bone loss, and occurs when the body's immune system attacks lining of the joints. In severe cases, internal organs can be attacked. Signs/symptoms of RA include but are not limited to joint stiffness, loss of energy, low grade fever, loss of appetite, dry eyes and/or mouth, firm lumps referred to as rheumatoid nodules that grow beneath the skin in places such as the elbows and hands, among others.

Rheumatoid factor (RF): Refers to antibodies directed against the Fc (fragment crystallizable region) fragment of immunoglobulin G (IgG). The antibodies referred to as RFs are heterogeneous and generally are comprised of immunoglobulin M (IgM). RFs are used as a marker in individuals with suspected RA or other autoimmune conditions.

Sample (biological sample): A biological specimen containing genomic DNA, RNA (including mRNA), protein, or combinations thereof, obtained from a subject. Examples include, but are not limited to, blood (serum and/or plasma), urine, saliva, milk, and the like. In one example, the sample includes serum and/or plasma from a subject suspected of being afflicted with RA.

Signs or symptoms: Any subjective evidence of disease or of a subject's condition, e.g., such evidence as perceived by the subject; a noticeable change in a subject's condition indicative of some bodily or mental state. A "sign" is any abnormality indicative of disease, discoverable on examination or assessment of a subject. A sign is generally an objective indication of disease. Signs include, but are not limited to any measurable parameters such as tests for detecting RA, including antibody blood tests, for example, tests for one or more of RF, ACPAs, ACA, antinuclear antibodies (ANA), and the like. Other tests include complete blood count (CBC), erythrocyte sedimentation rate, tests for C-reactive protein levels, imaging tests (e.g., X-ray and/or magnetic resonance imaging (MRI)) to provide a detailed picture of joints, and the like.

Streptavidin: A protein with an extraordinarily strong affinity for biotin (also known as vitamin B7 or vitamin H). Streptavidin as discussed herein may comprise an oligomer of streptavidin, streptavidin mutein or analog, avidin, an avidin mutein or analog (such as neutravidin) or a mixture thereof. In general, streptavidin naturally occurs as a tetramer of four identical subunits, i.e. it is a homo-tetramer, where each subunit contains a single binding site for biotin, a biotin derivative or analog or a biotin mimic.

Subject: A term that includes both human and veterinary individuals, for example mammals, such as humans.

Therapeutic agent: A substance that demonstrates some therapeutic effect by restoring or maintaining health, such as by alleviating one or more signs or symptoms associated with a disease or physiological disorder, or delaying (including preventing) progression or onset of a disease. In some instances, the therapeutic agent is a chemical or pharmaceutical agent, or a prodrug. A therapeutic agent may be an antirheumatic agent.

A "therapeutically effective amount" or "therapeutically effective dose" refers to an amount or dose sufficient to inhibit or prevent onset or advancement, to treat outward symptoms, or to cause regression, of a disease. The therapeutically effective amount or dose also can be considered as that amount or dose capable of relieving symptoms caused by the disease. Thus, a therapeutically effective amount or dose of an antirheumatic agent is that amount or dose sufficient to achieve a stated therapeutic effect. As one specific, non-limiting example, a therapeutically effective amount of an antirheumatic agent is an amount that reduces the signs of, symptoms of, or laboratory findings associated with RA; delays the progression of RA; or lowers one or more of biomarker level(s) associated with RA, inflammation associated with RA, and the like.

Treating a disease: A therapeutic intervention that ameliorates a sign or symptom of a disease or pathological condition including but not limited to a RA, such as a sign or symptom of RA. Treatment can induce remission or cure of a condition or slow progression, for example. In some instances, treating a disease can include inhibiting the full development of a disease, for example preventing development adverse conditions associated with RA. Prevention of a disease does not require a total absence of disease. For example, treating a disease can be a reduction in severity of some or all clinical symptoms of the disease or condition, a reduction in the number of relapses of the disease or condition, an improvement in the overall health or well-being of the subject, decrease in other parameters well known in the art that are specific to the particular disease or condition, and combinations of such factors. Discussed herein, "treating" a disease is interchangeable with "managing" a disease, such as RA.

III. Devices and Methods of Use for RA Biomarker Detection and Management of RA

In embodiments, anti-citrullinated HSA autoantibody levels may be assessed using a lateral flow device. Various lateral flow assay methods may be utilized to test for the presence or absence or quantity of an analyte, such as anti-citrullinated HSA autoantibody bound to citrullinated HSA, in a biological sample. For example, a "sandwich" assay method of the present disclosure may rely on one or more antibodies (or in some examples other recombinant proteins) immobilized on a solid support, which forms part of a complex that includes a labeled antibody or other labeled biomolecule. This may enable an ability to determine detection of the target analyte or target analyte complex by measuring a presence, and in some examples amount, of the target analyte-labeled antibody complex. In examples, the label may be colloid gold particles, however other labels are within the scope of this disclosure. Examples include but are not limited to enzymes, fluorescently-labeled microspheres, colored microspheres, and the like, provided the label enables detection and/or quantification of analyte bound to a test line.

Accordingly, lateral flow test strips of the present disclosure comprise a solid support on which sample receiving area (e.g., sample pad) and target capture zones (e.g., capture pad) are supported. The solid support material is one which is capable of supporting the sample receiving area and target capture zones and providing for the capillary flow of sample out from the sample receiving area to the target capture zones when the lateral flow test strip is exposed to an appropriate solvent or buffer which acts as a carrier liquid for the sample. General classes of materials that may be used as support include organic or inorganic polymers, and natural and synthetic polymers. More specific examples of suitable solid supports include, without limitation, glass fiber, cellulose, nylon, crosslinked dextran, various chromatographic papers and nitrocellulose. One particularly useful material is nitrocellulose.

Turning to FIG. 1, depicted is a schematic diagram showing an example of a lateral flow immunoassay 100 that may be used in accordance with various embodiments disclosed herein. In the example shown at FIG. 1, an antibody cocktail 101 comprising one or more of anti-human IgA, IgM and IgG is immobilized on a test line (not specifically shown at FIG. 1), and biotin-coupled bovine serum albumin (BSA) 102 is immobilized on a control line (not specifically shown at FIG. 1), of a membrane 103 (e.g., nitrocellulose membrane). An anti-HSA antibody 104 is coupled to a label 105 (e.g. colloidal gold particles) that serves as a test detector. The anti-HSA antibody 104 binds to, and hence detects, anti-citrullinated HSA autoantibody 113 bound to citrullinated HSA 114 that has been captured by the antibody cocktail 101. Streptavidin 106 coupled to another label 107 (e.g., colloidal gold particle) serves as the control detector by binding to the biotin 109 coupled to BSA 110 on the control line.

Figure 2B:
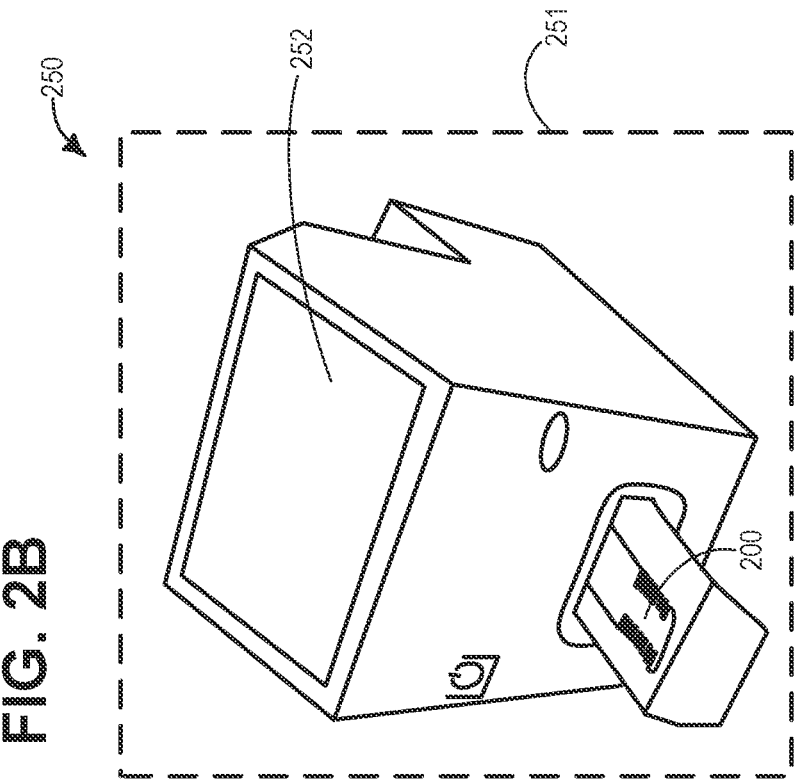
FIG. 2B depicts an illustration of an example reader device for quantification of test line intensity corresponding to lateral flow test devices of the present disclosure.
Figure 2A:
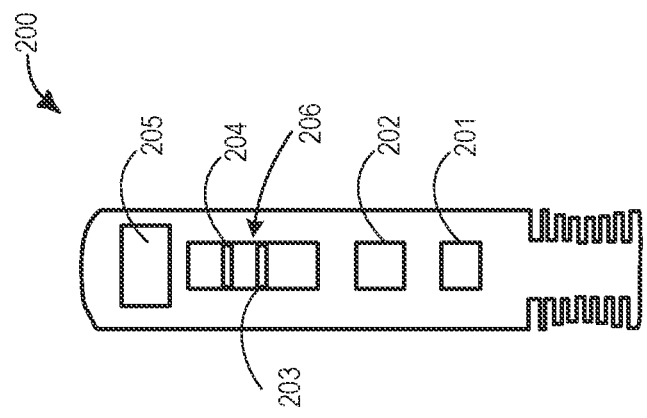
FIG. 2A depicts a lateral flow test device that may be used in accordance with various embodiments disclosed herein.

FIG. 2A depicts an example lateral flow test strip that may be used in accordance with various embodiments herein disclosed. The lateral flow test strip includes at least sample well 201 (also referred to herein as a sample pad), conjugate pad 202, capture pad 206 which includes test line 203 and control line 204, and optionally, absorption pad 205. In embodiments, labeled anti-HSA antibody (e.g., anti-HSA antibody 104 at FIG. 1) and labeled streptavidin (e.g., streptavidin 106 at FIG. 1) are dried onto conjugate pad 202. The conjugate pad may be treated with a solution that may include but is not limited to sodium borate, dextran, BSA, Tween-20, sodium azide, and the like. In examples, such a solution may be in a pH range of 7.5-8.5, for example pH 8.0. The drying of the labeled anti-HSA antibody and the labeled streptavidin may be conducted at temperatures ranging from 40-60° C., for example 50° C.

A biological sample, for example blood (e.g., serum or plasma), saliva, urine, milk, and the like, may in some examples be diluted in an appropriate buffer (e.g., running buffer comprising one or more of HEPES, CaCl2, NaCl, NaN3, Tween-20 and 0.01% polyvinyl alcohol), and applied to sample pad 201. Following sample application to sample pad 201, capillary action allows the components of the sample to hydrate and (potentially) interact with labeled anti-HSA antibody, as well as to hydrate the labeled streptavidin, at the conjugate pad 202. In embodiments that encompass the immunoassay detailed above at FIG. 1, labeled-anti-HSA antibody binds to citrullinated HSA-anti-citrullinated HSA autoantibody complex, and the formed immunocomplex may then further migrate to test line 203, where the complex may be captured by the immobilized antibody cocktail, via the antibody cocktail binding to anti-citrullinated HSA autoantibodies. Furthermore, the labeled streptavidin may migrate past the test line to the control line, to be captured by the biotin (e.g., biotin 109 at FIG. 1) coupled to BSA (e.g., BSA 110).

Turning to FIG. 2B, following completion of the capillary migration, the lateral flow test strip 200 may be scanned via a reader device 250. Reader 250 may utilize image analysis for quantification of relative amounts of labeled anti-HSA antibody at the test line and labeled streptavidin at the control line. As an example, in the case of colloidal gold labels, reader 250 may be configured to quantify intensity of a particular color (e.g., red color reflected by the colloidal gold particles) corresponding to the control line and the test line.

Accordingly, reader 250 may comprise an image analysis system 251. Image analysis system 251 may include but is not limited to one or more of a camera (e.g., CCD camera), lens (e.g., micro lens), light source (e.g., white light-emitting diode (LED) source), a light controller (e.g., LED controller) and a computing device (e.g., computer). Software programs stored on a memory of the computer may be used to analyze images acquired by image analysis system 251. As a non-limiting example, a software program or programs may be used to measure maximum peak area values of the test line and control line within a detection area of the lateral flow test strip. For example, peak area may be calculated by adding intensity values under an intensity profile of the test line or control line. Intensity associated with the control line may be used as a normalizing factor, such that experimental results may be expressed as the peak area of the test line divided by the peak area of the control line. The description as to how the image analysis system 251 operates is meant to be illustrative and non-limiting in nature. Accordingly, other components and/or methodologies of image analysis may be substituted for the above, without departing from the scope of this disclosure, provided that the particular image analysis system is able to determine a quantifiable relationship between the test line and the control line. In examples, reader 250 may include a display 252 that enables a user to interact with the reader 250 and corresponding image analysis system 251, to control one or more parameters for acquiring and/or processing images. Further, while not explicitly illustrated, in examples image reader 250 may include a recognition module for test and lot-specific calibration and quantification of each lateral test strip. For example, the recognition module may be capable of recognizing/decoding information stored in a quick response (QR) code, attached to each lateral flow test strip.

The lateral flow immunoassay depicted at FIG. 1 is advantageous in that the detection methodology does not necessitate the generation of anti-citrullinated HSA antibodies, but instead relies on anti-HSA antibodies that are readily available and can be used across a wide sample population. Specifically, it is herein recognized that in no case may subjects have circulating anti-native HSA autoantibodies, as autoantibodies are just generated within subjects to anti-citrullinated HSA and not non-citrullinated HSA. Thus, in no case will the lateral flow assay of FIG. 1 be capable of binding and immobilizing HSA protein unless the HSA protein is citrullinated, and hence, can bind the immobilized antibody cocktail (e.g., antibody cocktail 101 at FIG. 1) by way of the anti-citrullinated HSA autoantibodies (e.g., anti-citrullinated HSA autoantibodies 113 at FIG. 1). Accordingly, the only protein that the lateral flow assay depicted at FIG. 1 can detect is anti-citrullinated HSA in complex with anti-citrullinated HSA autoantibodies, even though the detection antibody is labeled anti-HSA and not specifically labeled anti-citrullinated HSA.

Figure 3:
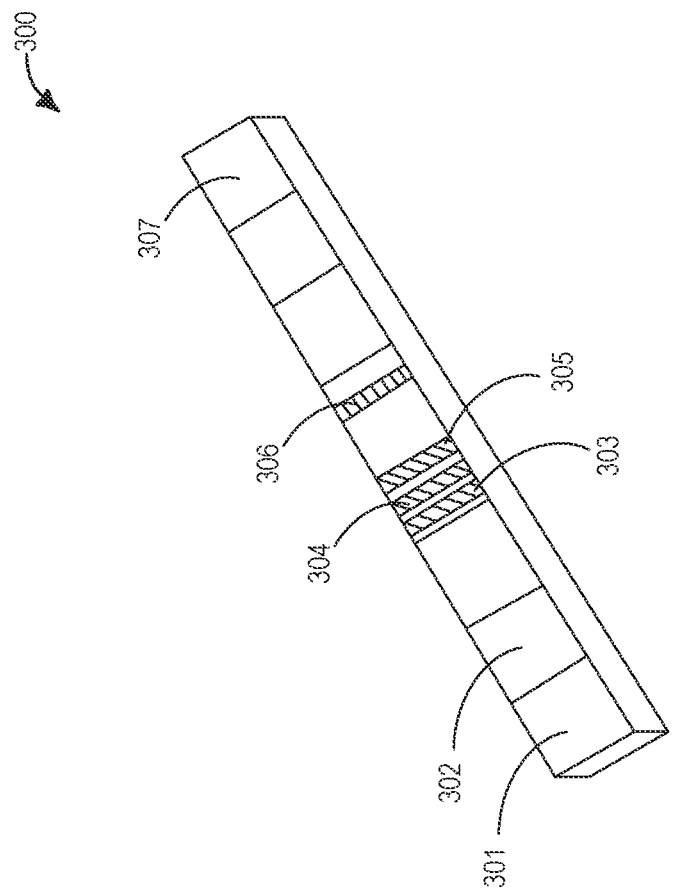
FIG. 3 depicts another lateral flow test device that may be used in accordance with various embodiments disclosed herein.

In another embodiment of a lateral flow device, there may be second, or third or even fourth (or more) test lines. It is herein recognized that this type of lateral flow device may enable determination of relative quantities of at least two of RF, ACPAs, and ACAs, in an example. Determination of relative quantities of at least two of RF, ACPAs, and ACAs may improve an ability to diagnose and/or manage RA. For example, the presence of more than one biomarker of rheumatic disease (e.g., RA) and the relative quantities of such biomarkers in relation to each other may be indicative of an increased risk and/or more severe progression of rheumatic disease (e.g., RA), which in turn may be relied upon for management of the rheumatic disease. Turning to FIG. 3, an example of a multi-test line lateral flow device 300, is shown. In the example at FIG. 3, three different test lines comprising first test line 303, second test line 304, and third test line 305, are included. Also illustrated is control line 306, sample pad 301, conjugate pad 302 and absorption pad 307. The operation of this particular embodiment is similar to that described above with regard to FIGS. 2A-2B, with some additional considerations. Specifically, a second detector reagent (e.g., another antibody conjugated to a detectable label) specific for a second analyte may be included in the conjugate pad 302, and the second test line 304 may include a second specific binding partner having affinity for a second analyte (e.g., ACPA). Similarly a third detector reagent (e.g., another antibody conjugated to a detectable label) specific for a third analyte may be included in the conjugate pad 302, and the third test line 305 may include a third specific binding partner having affinity for the third analyte (e.g., RF). In the example discussion above, the first test line 303 may comprise the antibody cocktail (e.g., antibody cocktail 101) immobilized on the test line for capture of anti-citrullinated HSA antibody (e.g., 113) bound to citrullinated HSA (e.g., 114) as discussed above with regard to FIG. 1. In another embodiment, elaborated below, the first test line may comprise citrullinated HSA. In some embodiments, the first, second, and third detector reagents may be the same, whereas in other embodiments one or more of the first, second, and/or third detector reagents may be different.

In an embodiment, as discussed, the first test line may comprise a test line for ACA, the second test line may comprise a test line for ACPA, and the third test line may comprise a test line for RF. In an example, the ACPAs may recognize mutated and citrullinated vimentin (MCV), and this aspect may be used in the lateral flow detection scheme. In other examples, one or more citrullinated peptides (including or excluding MCV) may be recognized by ACPAs, and this aspect may be used in the lateral flow detection scheme. In additional or alternative examples, RF may be recognized via a purified Fc-part of human immunoglobulin, and this aspect may be used in the lateral flow detection scheme. In this way, relative amounts of RF, ACPAs and ACAs may be determined on a single lateral flow device.

In some examples, lateral flow devices of the present disclosure may be prepared differently than the above example that includes three test lines. For example, in some cases, a lateral flow device may detect just one biomarker for RA, or just two biomarkers for RA. For example, a lateral flow device of the present disclosure may be configured to just detect ACA, via the methodology discussed with regard to FIG. 1 and not be additionally configured to test other RA biomarkers (e.g., RF and/or ACPA).

In some examples, a lateral flow device may be configured to detect just RF and ACPA. In such an example, purified recombinant MCV and purified Fc-part of human immunoglobulin may be immobilized at each of the second test line and third test line, respectively. A detector label (e.g., colloidal gold particles) may be conjugated individually to goat anti-human IgG and IgM, and applied to the conjugate pad. Other examples are within the scope of this disclosure. For example, a lateral flow device may be configured to detect ACA and RF but not ACPA. In another example, a lateral flow device may be configured to detect ACA and ACPA but not RF.

In the above examples where at least two RA biomarkers are detectable on a single lateral flow device, the control line (e.g., control line 306) may be configured in similar fashion as that discussed with regard to FIG. 1 (e.g., striped with biotin-conjugated BSA), for detection via labeled streptavidin, however other alternatives for controls are within the scope of this disclosure. For example, the control line may be striped with anti-goat IgG, or protein L. Other examples are within the scope of this disclosure.

In a representative example where at least two RA biomarkers are detectable on a single lateral flow device, such a lateral flow device may be configured as follows. Specifically, the first test line (e.g., test line 303 at FIG. 3) may be configured to detect ACA, the second test line (e.g., test line 304 at FIG. 3) may be configured to detect ACPA, and the third test line (e.g., test line 305 at FIG. 3) may be configured to detect RF. The first test line may be striped with (e.g., may comprise) citrullinated HSA, the second test line may be striped with a citrullinated peptide mixture including or excluding MCV, and the third test line may be striped with the purified Fc-part of human immunoglobulin. One or more of the citrullinated HSA, citrullinated peptide mixture, and/or Fc-part of human immunoglobulin may be recombinantly produced and purified for striping of the corresponding test lines of the lateral flow device. The control line may comprise one or more of anti-goat IgG, protein L, and the like. In such an example, the detector may comprise a goat-anti-human IgG, IgM and IgA coupled to a detectable label. The detectable label may comprise one or more of fluorescent tags/particles, enzymatic linkages, radioactive isotopes, microspheres, and nanoparticles. In one representative embodiment, the detectable is colloidal gold particle(s). In this way, at least two (e.g., 3) RA biomarkers may be detectable on a single lateral flow device.

Sample pads as discussed (e.g., 201) are components of lateral flow devices of the present disclosure. The sample pads initially receive the sample (e.g., biological sample), and may serve to remove particulates from the sample. Among the various materials that may be used to construct a sample pad (such as glass fiber, woven fibers, screen, non-woven fibers, cellulosic fibers or paper), a cellulose sample pad may be beneficial if a large bed volume (e.g., 250 µl/cm2) is a factor in a particular application. Sample pads may be treated with one or more release agents, such as buffers, salts, proteins, detergents, and surfactants. Such release agents may be useful, for example, to promote resolubilization of conjugate-pad constituents, and to block non-specific binding sites in other components of a lateral flow device, such as a nitrocellulose membrane. Representative release agents include, for example, trehalose or glucose (1%-5%), PVP or PVA (0.5%-2%), Tween 20 or Triton X-100 (0.1%-1%), casein (1%-2%), SDS (0.02%-5%), and PEG (0.02%-5%).

The conjugate pads (e.g., 202) of the present disclosure serve to, among other things, hold a detector reagent. Suitable materials for the conjugate pad include glass fiber, polyester, paper, or surface modified polypropylene. In some embodiments, a detector reagent may be applied externally, for example, from a developer bottle, in which case a lateral flow device need not contain a conjugate pad (see, for example, U.S. Pat. No. 4,740,468).

Detector reagent(s) contained in a conjugate pad is typically released into solution upon application of the test sample. A conjugate pad may be treated with various substances to influence release of the detector reagent into solution. For example, the conjugate pad may be treated with PVA or PVP (0.5% to 2%) and/or Triton X-100 (0.5%). Other release agents include, without limitation, hydroxypropylmethyl cellulose, SDS, Brij 35, and β-lactose. A mixture of two or more release agents may be used in any given application. In a particular disclosed embodiment, the detector reagent in conjugate pad is a gold-conjugated antibody, or a plurality of different gold-conjugated antibodies. In some examples, different antibodies serving as different detectors may be labeled with different detector labels.

The use of an absorption pad (e.g., 205) in lateral flow devices of the present disclosure may be optional. The absorbent pad acts to enable an increase in the total volume of sample that enters the device. This increased volume can be useful, for example, to wash away unbound analyte from the membrane. Any of a variety of materials is useful to prepare an absorbent pad, for example, cellulosic filters or paper. In some device embodiments, an absorbent pad can be paper (i.e., cellulosic fibers). One of skill in the art may select a paper absorbent pad on the basis of, for example, its thickness, compressibility, manufacturability, and uniformity of bed volume. The volume uptake of an absorbent made may be adjusted by changing the dimensions (usually the length) of an absorbent pad.

Figure 4:
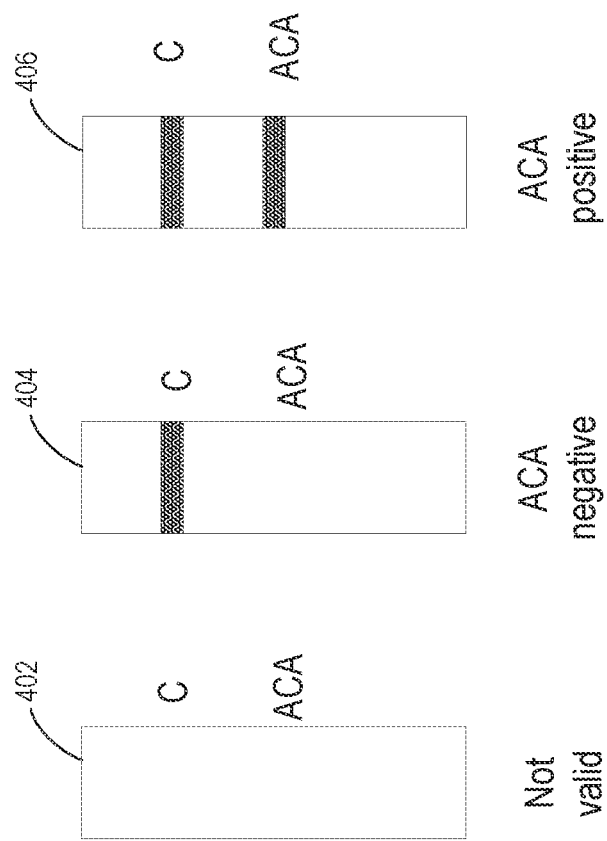
FIG. 4 illustratively depicts example results of a lateral flow test device such as that depicted at FIG. 2A.

Turning now to FIG. 4, depicted are illustrative examples of results that can be obtained from a lateral flow device that includes one test line for detection of ACA, and a control line. Shown on the left is an example of an invalid test, lacking significant signal at both the control line and the test line. The middle illustration depicts a lateral flow device that shows a valid test with a negative result for ACA. Specifically, a signal is observed at the control line but not at the ACA test line, hence the biological sample used for testing is negative for ACA in the middle illustration. The illustration on the right depicts a lateral flow device that shows a positive result for ACA. Specifically, a signal is observed at both the control line and the ACA test line, indicating that the biological sample used for testing is positive for ACA in the illustration on the right at FIG. 4.

As discussed above with regard to FIGS. 2A-2B, the lateral flow devices of the present disclosure may be read by a reader (e.g., reader 250), to enable quantitation of an amount of ACA in the biological sample. As will be elaborated in greater detail below, particulars of RA management may be different depending on levels of ACA detected. Briefly, an effective amount of a therapeutic agent (e.g., antirheumatic agent) provided to a subject to manage RA (e.g., alleviate at least one sign or symptom of RA) may be different as a function of ACA amount determined in the biological sample. Additionally or alternatively, a particular therapeutic agent or agents may be used as a function of one ACA amount (e.g., one amount range) determined in a biological sample, and a different therapeutic agent or agents may be used for another ACA amount (e.g., another amount range), to alleviate at least one sign or symptom of RA. In still other additional or alternative examples, managing RA may include one or more particular antirheumatic lifestyle modifications, which may be a function of a determined amount of ACA in a biological sample. As examples, less aggressive treatment management may be used when lesser amounts of ACA are detected, and more aggressive treatment management may be used when greater amounts of ACA are detected. Less aggressive treatments can include but are not limited to lower dosages of therapeutic agents (e.g., antirheumatic agents), lesser numbers (e.g., different types) of therapeutic agents provided to the subject, and less stringent behavioral lifestyle modifications (e.g., less restrictive diet, lesser emphasis on exercise, and the like), as compared to more aggressive treatments.

Figure 5:
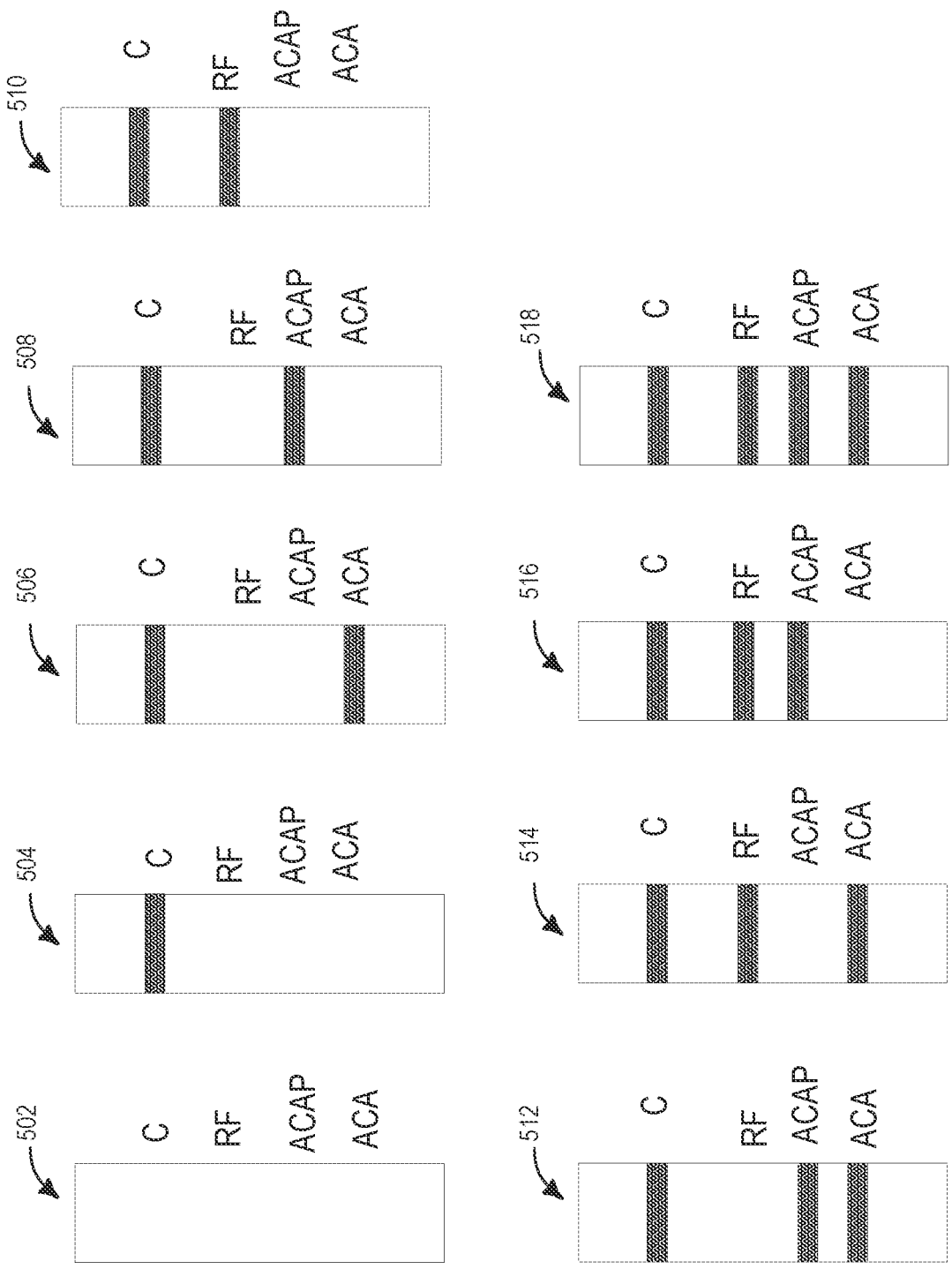
FIG. 5 illustratively depicts example results of a lateral flow test device such as that depicted at FIG. 3.

Turning to FIG. 5, depicted are a series of lateral flow devices showing example results in an example where the devices are capable to detect a plurality of RA biomarkers. In the examples shown, the biomarkers detectable include ACA, RF and ACPA.

Device 502 illustrates an example of an invalid test, as none of the biomarkers are detected, nor is a control signal detected. Device 504 illustrates an example of a valid test for which a biological sample is negative for each of RA, ACA and ACPA. Device 506 illustrates an example of a valid test for which a biological sample is positive for ACA, but negative for ACPA and RF. Device 508 depicts an example of a valid test for which a biological sample is positive for ACPA, but negative for ACA and RF. Device 510 depicts an example of a valid test for which a biological sample is positive for RF, but negative for ACA and ACPA. Device 512 depicts an example of a valid test for which a biological sample is positive for both ACA and ACPA, but negative for RF. Device 514 depicts an example of a valid test for which a biological sample is positive for ACA and RF, but negative for ACPA. Device 516 depicts an example of a valid test for which a biological sample is positive for ACPA and RF, but negative for ACA. Device 518 depicts an example of a valid test for which a biological sample is positive for each of ACA, ACPA and RF.

The depicted examples at FIG. 5 are shown for illustrative purposes. It may be understood that, similar to that discussed above with regard to FIG. 4, a reader (e.g., reader 250) may be capable of quantifying relative amounts of biomarker detection in a case where a plurality of biomarkers are examined. Thus, test results may not simply be "positive" or "negative" for particular biomarkers, but quantifiable levels of the biomarkers in a biological sample may be capable of being determined. As an illustrative example, a biological sample tested on a lateral flow device of the present disclosure may detect all three of RF, ACPA and ACA, with RF being three times as abundant as ACPA, which in turn may be two times as abundant as ACA. Such an example is meant to be illustrative and non-limiting, and a wide variety of potential results are within the scope of this disclosure. By determining relative amounts of each of RF, ACPA and ACA to one another, management of RA may be improved at various stages of RA. For example, selection of one or more of particular amount of therapeutic agent (e.g., antirheumatic agent) or agents, particular type of therapeutic agent or agents, particular recommendations as to antirheumatic lifestyle modifications, etc., may be differentially provided for managing RA as a function of a determination of relative amounts of RF, ACPA and ACA as detected via a lateral flow device of the present disclosure capable of such determination. While not explicitly illustrated, in other examples where less than three biomarkers (e.g., 2) are detected via a lateral flow device, similar methodology may be used to determine relative abundance, and management of rheumatic disease (e.g., RA) may be adjusted according to the determined relative abundances.

In particular embodiments, the lateral flow device described above with regard to at least FIG. 1 and FIG. 2A may be used for a rapid point-of-care test for RA. In other words, a lateral flow device capable of rapidly providing results as to ACA levels in a biological sample may enable rapid assessment of RA and rheumatic disease. As an example, such a lateral flow device may enable quantitation of an amount of ACA in a biological sample of a subject, which in turn may be used to assess severity of disease and/or predict a rate at which rheumatic disease progression may occur.

In embodiments, one or more thresholds pertaining to ACA levels (e.g., titer) in a biological sample may be relied upon in order to effectively manage rheumatic disease (e.g., RA). As an example, a first threshold, a second threshold, and a third threshold may be used, where ACA levels below the first threshold are used to manage RA in a first manner, where ACA levels greater than the first threshold but below the second threshold are used to manage RA in a second manner, where ACA levels greater than the second threshold but lower than the third threshold are used to manage RA in a third manner, and where ACA levels greater than the third threshold are used to manage RA in a fourth manner. As examples, the first manner may be a less aggressive course of action than the second manner, which is in turn is a less aggressive course of action than the third manner, which in turn is a less aggressive course of action than the fourth manner. Lesser aggressive courses of action may include one or more of lesser amounts of therapeutic agents, greater duration between treatments with therapeutic agents, use of lesser numbers of different therapeutic agents, selection of different types of therapeutic agents as compared to more aggressive courses, and less stringent antirheumatic lifestyle modifications. In some examples, ACA levels below the first threshold may warrant no course of action in terms of managing RA, with increasingly aggressive courses of action increasing upon ACA levels passing the first threshold, the second threshold, or the third threshold.

For example, ACA levels discussed herein may range from about 100 U/mL to about 3500 U/mL. In examples, the first ACA threshold may comprise about 500 U/mL, the second ACA threshold may comprise about 1000 U/mL, and the third threshold may comprise about 2000 U/mL. Differential management of rheumatic disease (e.g., RA) may be provided depending on, as mentioned above, whether ACA levels are below the first threshold (e.g., about 500 U/mL or less), greater than the first threshold but lower than the second threshold (e.g., within a range of about 500 U/mL to about 1000 U/mL), greater than the second threshold but lower than the third threshold (e.g., within a range of about 1000 U/mL to about 2000 U/mL), or greater than the third threshold (e.g., greater than about 2000 U/mL).

Similar logic applies to tests in which levels of at least two biomarkers (e.g., ACA and ACPA, or ACA and RF), or even three biomarkers (e.g., ACA, RF and ACPA) are used in terms of managing RA. In such an example, relative levels of two biomarkers with respect to one another may be relied upon for managing RA. In another example, relative levels of three biomarkers with respect to one another may be relied upon for managing RA. For example, depending on relative levels of at least two biomarkers with respect to one another, an effective amount of one or more antirheumatic agents may selected to effectively manage RA in order to cause a reduction in at least one sign or symptom associated with RA. Additionally or alternatively, relative levels of at least two biomarkers with respect to one another may be relied on for determining one or other parameters for management of RA, for example one or more antirheumatic lifestyle modifications. Furthermore, a determination of relative levels of two or more RA biomarkers with respect to one another for effectively managing RA need not necessarily be on a same lateral flow device. As one example, a first lateral flow device may be capable of detecting and quantifying ACA, while a second lateral flow device may be capable of detecting and quantifying RF and/or ACPA. In such an example, quantification may be normalized to control levels as discussed, to enable comparison of relative levels of at least two RA biomarkers between lateral flow test devices.

Still further, a determination of relative levels of two or more RA biomarkers with respect to one another need not necessarily be confined to just lateral flow assays. Examples of other assays for RF and ACPA have been described herein, and it is within the scope of this disclosure to rely on such assays in order to determine relative levels of at least two biomarkers with respect to each other. In one illustrative example, a lateral flow device of the present disclosure may be used to determine ACA levels, which in turn may be compared with RF and ACPA levels obtained by other assay formats (e.g., ELISA) not including lateral flow assay formats.

EXAMPLES

Example 1

Anti-Citrullinated Albumin Antibodies in Bodily Fluids from Rheumatic Disease

In a prospective study, serum or plasma samples were collected from 156 patients with either suspected or diagnosed rheumatic disease. RF, ACPA, and ACA were measured. 95 subjects were positive for RF (sensitivity of 60% positive), 75 subjects were positive for ACPA (sensitivity of 48% positive) and 61 subjects were positive for ACA (sensitivity of 39% positive).

In another separate cross-sectional study, 855 banked serum or plasma control samples from populations in 4 different countries were tested for ACA. 853 subjects were negative for ACA and 2 were positive, representing a specificity of 99.8%. In examples, data can be represented as a negative predictive value, or in other words a probability that subjects with a negative screening test do not actually have the disease (or biomarker associated with the disease). Reliance on one or more of specificity and negative predictive value may be beneficial in terms of screening a general population to identify potential subjects with risk for RA.

Example 2

Clinical Validation of an Anti-Citrullinated Albumin Antibody (ACA) Point-of-Care Test for Rheumatoid Arthritis vIn a prospective study, serum samples were collected from 284 patients diagnosed with rheumatic disease to assess the performance of an ACA point-of-care test and compare it with the current standard anti-cyclic citrullinated peptide (ACCP) assay. The rheumatic disease cohort included 242 subjects with rheumatoid arthritis, 6 subjects with psoriatic arthritis, 6 subjects with spondyloarthropathies, 18 subjects with lupus, 4 subjects with gout, 6 subjects with HLA B27 positive, 1 subject with osteoarthritis, and 1 subject with polyarthritis. In one example, the ACA point-of-care test may be performed by using the lateral flow test device depicted in FIG. 2A.

A summary of results of the ACA and ACCP tests is shown in Table 1, below.

TABLE 1

ACA and ACCP test results

| Diagnosis | Anti-citrullinated albumin antibodies (ACA) assay. Positive/Total | Anti-cyclic citrullinated peptide (ACCP) assay. Positive/Total |
|---|---|---|
| Rheumatoid arthritis | 109/242 (45%) | 112/242 (46%) |
| Psoriatic arthritis | 0/6 | 0/6 |
| Spondyloarthropathies | 0/6 | 0/6 |
| Lupus | 5/18 | 4/18 |
| Gout | 1/4 | 1/4 |
| HLA B27 positive | 0/6 | 0/6 |
| Osteoarthritis | 0/1 | 0/1 |
| Polyarthritis | 0/1 | 1/1 |

ACCP-negative and ACA-positive = 28 subjects (unique to ACA)
ACCP-positive and ACA-negative = 31 subjects (unique to ACCP)
ACCP-positive + ACA-positive = 140 subjects (58%)

Figure 6:
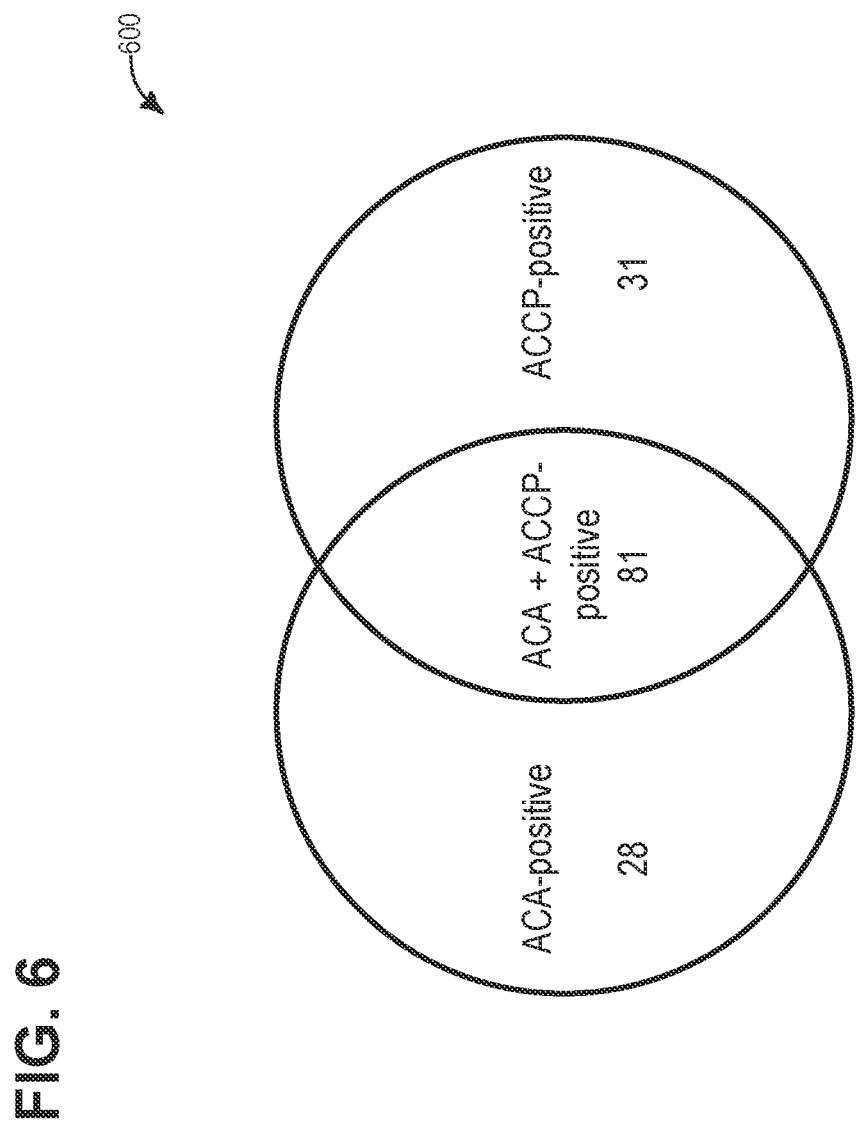
FIG. 6 depicts a Venn diagram for anti-citrullinated albumin antibodies (ACA) positive subjects and anti-cyclic citrullinated peptide (ACCP) positive subjects in a clinical study for rheumatoid arthritis.

Table 1 indicates that out of 242 subjects with rheumatoid arthritis, 109 subjects were positive with the ACA test (sensitivity of 45% positive) and 112 subjects were positive with the ACCP test (sensitivity of 46% positive). As depicted by Venn diagram 600 shown in FIG. 6, 28 subjects were positive with the ACA test but negative with the ACCP test, and 31 subjects were positive with the ACCP test but negative with the ACA test. As indicated in FIG. 6, 81 subjects were positive with both the ACA and ACCP tests. Thus, overall 140 (i.e., 58%) of the 242 rheumatoid arthritis subjects were positive with a combination of the ACA and ACCP tests compared to 112 (i.e., 48%) that were positive with the ACCP test alone.

Therefore, the rheumatoid arthritis (RA) autoimmune marker ACA identifies a subset of RA patients not detected by the ACCP assay and increases the sensitivity of detection in combination with the ACCP assay. Furthermore, ACA-positive subjects may be associated with severe/progressive disease because of citrullination of a major serum protein. Thus, the addition of ACA testing to the current standard ACCP testing may increase the rate of detection and indicate potential for more severe disease.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method of detecting and quantifying anti-citrullinated human serum albumin (HSA) autoantibody in a biological sample, comprising:
   obtaining the biological sample from a subject;
   applying the biological sample to a lateral flow device, wherein the lateral flow device comprises anti-human IgA, IgG, and IgM antibodies affixed to a surface, under conditions sufficient for formation of an immunocomplex, wherein the immunocomplex comprises anti-citrullinated HSA autoantibody bound to citrullinated HSA;
   applying to the lateral flow device an anti-HSA antibody coupled to a detectable label, wherein the anti-HSA antibody is capable of binding the citrullinated HSA in the immunocomplex; and
   detecting a quantity of the immunocomplex to determine a quantity of anti-citrullinated HSA autoantibody.

2. The method of claim 1, wherein the biological sample is serum or plasma.

3. The method of claim 1, wherein the detectable label is a colloidal gold particle.

4. The method of claim 1, wherein detecting the quantity of the immunocomplex is via a reader configured with an image analysis system; and
   wherein detecting the quantity of the immunocomplex further comprises quantifying relative amounts of the immunocomplex to a control complex.

5. The method of claim 4, wherein the control complex comprises streptavidin coupled to a detectable label.

6. The method of claim 5, wherein the detectable label of the control complex is a colloidal gold particle.

7. The method of claim 5, wherein the streptavidin coupled to the detectable label is captured via the lateral flow device by biotin-coupled bovine serum albumin (BSA).

8. A method of detecting and quantifying a first biomarker and at least a second biomarker associated with rheumatic disease in a biological sample of a subject, comprising:
   obtaining the biological sample from the subject;
   applying the biological sample to a lateral flow device, wherein the lateral flow device comprises anti-human IgA, IgG, and IgM affixed to a surface, under conditions sufficient for formation of a first immunocomplex comprising at least the first biomarker and a first labeled biomolecule capable of recognizing the first biomarker, wherein the first biomarker is anti-citrullinated human serum albumin (HSA) autoantibody, and the first labeled biomolecule is anti-HSA antibody coupled to a detectable label, and
   wherein the second biomarker is one of rheumatoid factor (RF), anti-cyclic citrullinated peptide autoantibody (ACCP), or anti-citrullinated peptide autoantibody (ACPA); and
   detecting a quantity of each of the first immunocomplex and the second biomarker.

9. The method of claim 8, further comprising a second immunocomplex comprising at least the second biomarker and a second labeled biomolecule capable of recognizing the second biomarker, and wherein detecting the second biomarker comprises detecting the second immunocomplex.

* * * * *